(12) United States Patent
Gundersen

(10) Patent No.: US 9,161,603 B2
(45) Date of Patent: Oct. 20, 2015

(54) PAD WITH FLUID BARRIER

(75) Inventor: Dag H. Gundersen, Tolvsrød (NO)

(73) Assignee: PadTech AS, Fornebu (NO)

( * ) Notice: Subject to any disclaimer, the term of this patent is extended or adjusted under 35 U.S.C. 154(b) by 1007 days.

(21) Appl. No.: 13/254,459

(22) PCT Filed: Mar. 1, 2010

(86) PCT No.: PCT/NO2010/000080
§ 371 (c)(1),
(2), (4) Date: Nov. 16, 2011

(87) PCT Pub. No.: WO2010/101472
PCT Pub. Date: Sep. 10, 2010

(65) Prior Publication Data
US 2012/0059339 A1 Mar. 8, 2012

(30) Foreign Application Priority Data
Mar. 3, 2009 (NO) .................................. 20090965

(51) Int. Cl.
| | |
|---|---|
| A61F 13/00 | (2006.01) |
| A45D 34/04 | (2006.01) |
| A45D 40/00 | (2006.01) |
| A61K 9/70 | (2006.01) |

(52) U.S. Cl.
CPC ............... *A45D 34/04* (2013.01); *A61F 13/00* (2013.01); *A45D 40/0087* (2013.01); *A45D 2200/1018* (2013.01); *A45D 2200/1036* (2013.01); *A61F 2013/00297* (2013.01); *A61F 2013/00906* (2013.01); *A61K 9/703* (2013.01)

(58) Field of Classification Search
CPC ...... A61M 35/00; B43M 11/06; A61K 9/703; A45D 2200/1018; A45D 2200/1036; A61F 2013/00297

USPC .......................................................... 604/304
See application file for complete search history.

(56) References Cited

U.S. PATENT DOCUMENTS

| | | | |
|---|---|---|---|
| 3,124,825 A | | 3/1964 | Iovenko |
| 3,580,254 A | * | 5/1971 | Stuart ............................ 604/290 |
| 4,896,768 A | * | 1/1990 | Anderson ...................... 206/210 |
| 5,480,646 A | | 1/1996 | Vu |
| 5,562,642 A | * | 10/1996 | Smith et al. .................... 604/289 |
| 5,773,022 A | * | 6/1998 | Nyqvist-Mayer ....... A61F 13/02 424/443 |

(Continued)

FOREIGN PATENT DOCUMENTS

| | | |
|---|---|---|
| CN | 100336494 | 9/2007 |
| DE | 3725180 | 1/1989 |

(Continued)

*Primary Examiner* — Susan Su
(74) *Attorney, Agent, or Firm* — Christian Abel

(57) ABSTRACT

The present invention relates to a device for applying at least one product in a controlled manner onto a surface. The device comprises several layers, where a bottom layer and at least a storage layer are welded together during the manufacturing of the device in order to create a temporary liquid barrier in the storage layer. The temporary liquid barrier will form at least one closed chamber in the storage layer, where the purpose of the temporary liquid barrier is to delay the liquid running over the barrier after the storage layer has been filled with the liquid that is to be applied. This delay of the liquid running over the temporary liquid barrier will ensure that the rest of the different layers of the device can be joined together inside and around their outer peripheries, in order to create a liquid tight storage chamber for the product.

12 Claims, 2 Drawing Sheets

(56) References Cited

U.S. PATENT DOCUMENTS

| | | | |
|---|---|---|---|
| 5,961,500 A | 10/1999 | Weinstein | |
| 6,000,403 A * | 12/1999 | Cantwell | 128/888 |
| 6,169,223 B1 * | 1/2001 | Mahr et al. | 602/56 |
| 7,240,790 B2 * | 7/2007 | Wendel et al. | 206/210 |
| 7,650,995 B2 | 1/2010 | Assie et al. | |
| 2003/0106812 A1 * | 6/2003 | Wilkman | 206/210 |
| 2005/0284777 A1 | 12/2005 | Wilkman | |
| 2006/0000734 A1 * | 1/2006 | Ninomiya | A61K 9/703 206/438 |
| 2010/0262090 A1 * | 10/2010 | Riesinger | 604/304 |
| 2010/0292660 A1 * | 11/2010 | Kydonieus | A61K 9/703 604/307 |

FOREIGN PATENT DOCUMENTS

| | | |
|---|---|---|
| FR | 2846635 | 5/2004 |
| WO | WO 00/48541 | 8/2000 |
| WO | WO03/000106 Y | 1/2003 |
| WO | WO 2005/115286 | 12/2005 |
| WO | WO 2007/065428 | 6/2007 |
| WO | WO 2009/009651 | 1/2009 |

\* cited by examiner

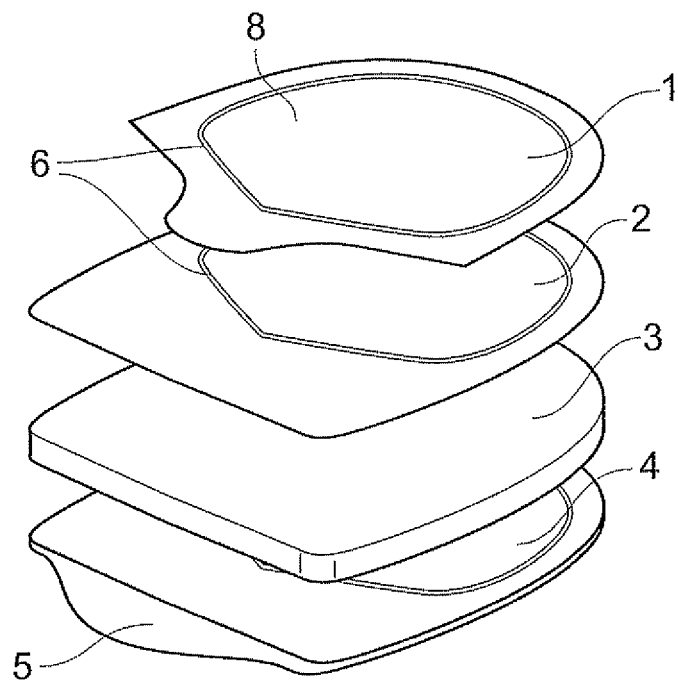
FIG. 1
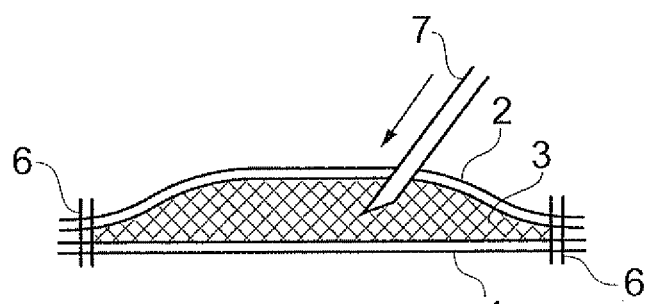
FIG. 2 - Prior art

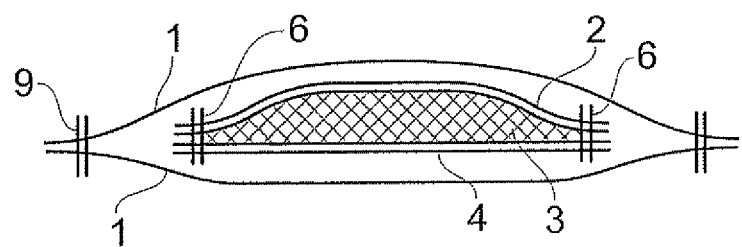
FIG. 3 - Prior art
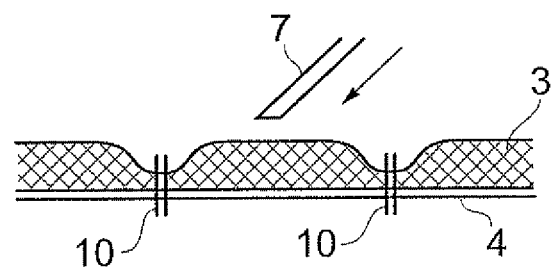
FIG. 4
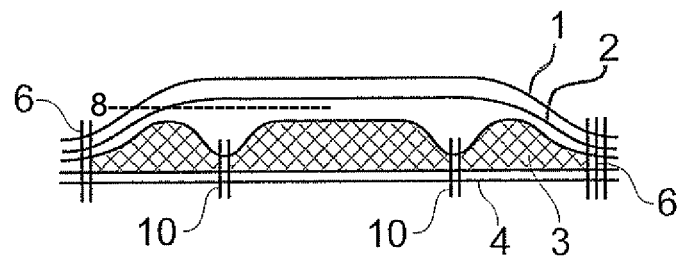
FIG. 5

PAD WITH FLUID BARRIER

The present invention relates to a device for applying at least one product at a desired place. More particularly, the present invention regards a pad accommodating at least one product, where the construction of the pad will ensure a correct filling of the device and where the product(s) will remain in its stored compartment, without the risk of leaking before the pad is to be used.

There are today different methods available for applying various liquids or colloidal substances, hereinafter referred to as a product, on a desired spot or surface. The product can for instance be applied to a surface by the user simply placing the product from a bottle or tube on their hand and then manually spread on the desired surface. This method is the most inexpensive, but it is also inefficient, messy and may result in a uneven application of the product. Furthermore, the bottles or tubes contain a fairly large quantity of the product and can therefore be inconvenient to carry with the user.

One other method is to have separate bottles and applicator elements. The applicator element will soak up some of the product when they are brought into contact with each other, whereby the user uses the applicator element to disperse the product over a desired spot or surface. This method may result in spillage when applying the product to the applicator element, and some of the product may also be wasted as the applicator element itself will absorb some of the product. A further problem with this method is that the product to be applied may come in contact with the user's hands, which is not desirable, especially if the product is irritating for the skin.

Yet another method for applying a product on a desired surface is to use a disposable or single-use applicator which is supplied with a pre-determined quantity of the product. Such applicators are manufactured from a disposable material substantially fully infused with the appropriate product, for example, a cleansing cream, and sealed in a container. This results in relatively costly manufacture, since a larger amount of the cosmetic product than is required is applied to the sheet of material. The applicator may also be so infused with the product to be applied that it will result in uneven application of the product on the desired surface. It will also be very difficult to control the amount of product transferred from the applicator to the skin, increasing the chance of excessive application of the product.

The above mentioned product can for instance be a liquid, such as wound cleansing agent, special cleansing liquid for various purposes such as, nail varnish, varnish remnants, glue remnants etc. and the colloidal substances can for instance be shoe cream, cosmetics, moisture creams, cleansing creams, self-tanning creams, various gel products for personal hygiene, soap etc. Furthermore, the product can be pharmaceutical products, such as pain relief, anti-itching agents etc.

A common feature of the applicators shown in the prior art is that they are neither economical or able to control the application of a product onto a surface.

U.S. Pat. No. 3,124,825 describes a nail polish remover, where there is provided a single use, disposable package including a container drawing positioned therebetween an applicator with enough polish remover impregnated therein to remove the polish from all the nails of a user. The package consists of a flexible pouch heat sealed at its free edges to form an envelope which seals material contained therein from contact with liquids or gases. Within the pouch is an applicator saturated with the nail polish remover.

U.S. Pat. No. 5,961,500 describes a prewetted medical wipe with impermeable barrier, where the wipe is constructed by bonding a layer of absorbent material to one side of a barrier sheet that is impermeable to infectious agents and insoluble in dermatological fluids, filling a reservoir in the barrier with a dermatological fluid, and hermetically sealing the absorbent layer between the barrier and a cover. The peripheral edges of the absorbent layer are spaced inwardly from the peripheral edges of the barrier to provide a surrounding zone of the impermeable barrier alone. The absorbent layer bond to the barrier is resistant to degradation caused by exposure to the dermatological fluid.

One of the disadvantages of the prior art is the lack of control of speed or direction which the flowable material is squeezed and discharged out of the package. Furthermore, due to its form of construction, there is no control of the flow from the package.

Furthermore, many of the known applicators also have a tendency to leak during the filling of the applicator and/or to leak after the applicator have been stored for a while.

It is therefore an object of the present invention to provide a device which can be filled with at least one product in a simple and economical way.

Another object of the present invention is to provide a device where the product or products will not leak and/or desiccate during storing and transportation.

A further object of the present invention is to provide an economical device for containing and dispensing a product or products to a surface in a convenient, uniform and simple manner.

Yet a further object of the present invention is to provide an applicator for products, in the form of a single product which minimizes and possibly alleviates the disadvantages normally associated with use of such products as currently applied, and help make their use easier and more effective.

These objectives are achieved with a device for applying a product onto a surface according to the invention as defined in the enclosed independent claim, where embodiments of the invention are given in independent claims.

According to the present invention a device is provided a device which can apply at least one product in a controlled manner onto a surface or a spot, where the device comprises several layers that are joined in appropriate ways. Each of the layers of the device has its own specific function.

The device according to the present invention is especially suitable for accommodating a product or products that are thin and/or having a low viscosity, as it in at least one of the layers of the device is provided a temporary barrier. The purpose of the temporary barrier is to delay the product from running over the barrier, whereby the layers can be joined together.

A typical device can for example consist of four layers, the layers being a bottom layer, a storage layer, a contact layer and a top layer sealing off the device. However, the device may also comprise fewer or more layers, where this will depend on which material is used for the different layers, the product(s) contained in the device, and for which purpose the device is manufactured etc.

The bottom layer constitutes the rear surface of the device, and serves to protect the storage layer from desiccation. It will also prevent the user from being soiled during use. In a preferred embodiment the bottom layer may also be manufactured as a pocket (comprising an additional outer elastic layer) or comprise a holding device, in order to ease the use of the device. The bottom layer may be manufactured from a liquid-impermeable material, for instance a plastic film that has good welding properties, in order to be attached to one or more of the other layers. The attachment between the different layer(s) may for instance be done by means of heat-seal, ultrasonic weld or adhesive to prevent its removal from the other layer(s).

The storage layer according to the present invention may be provided with a fibre structure with intersecting fibres, where the fibres can be situated in one or several layers. The structure of the fibres will form cavities of a size and shape that enable it to contain the specific product that has to be stored. The size of the cavities may vary depending on the viscosity of the product to be contained. As the structure substantially is not absorbent, it has to be dosed with or be supplied in another way with a product it has to contain.

The storage structure may also be manufactured from a material having a different cell structure, for instance a rubber sponge material or a non-woven material, having sufficient porosity to store the product to be applied.

The storage layer, due to the properties of the materials used, will have a "springy effect", where this will result in the storage layer releasing some of the product each time the device is compressed. When the pressure is relieved, the remaining product will be stored in the storage layer.

The cavities in the storage material may also be made artificially, as one for instance can use a needle, knife or the like, in order to form perforations and/or openings in the storage layer. This is important when a certain amount of a product is to be stored on a specific location in the pad.

The storage layer, together with one or more of the other layers, may also be manufactured as a multi chambered layer, where this for instance is advantageous when the storage layer contains two or more different products having different density and/or that are not to be mixed before the device is to be used. This "chambering" may be achieved by a welding forming a barrier between the chambers, where this barrier will burst or open when a certain pressure is applied to the storage layer.

In order to be able to fill the device with at least one product that is thin or has a low viscosity, a temporary barrier is created in the storage layer. During the filling of the product(s) in the storage layer, the temporary liquid barrier will delay the product running over the temporary liquid barrier, where this delay will be sufficient to join the rest of the layers of the device.

The contact layer, which is the layer that is in contact with the surface on which the product is to be applied, can be a film or a fabric (e.g. non-woven). The layer has a suitable structure which is selected according to the application for which the device is to be used. If the device, for instance, is used as a shoe cream applicator, then the contact layer will have a surface that is suited for spreading out and polishing the shoe when the shoe cream is applied. If, for instance, the device is used to cleanse skin with sterile cleansing liquid, the contact layer must then also have a surface that is soft against the skin and preferably have a desired degree of roughness to enable it to remove dirt etc. from the user's skin. In such cases the material must often be sterile before use and may therefore be protected by a separate layer that is torn off before use of the device.

The different layers in the device are in appropriate ways connected or attached together. In a preferred embodiment of the present invention the bottom layer, the storage layer, the contact layer and a top layer are attached to each other along an inside of their outer edges, thereby forming a sealed storage chamber. This attachment or connection between the different layers may for instance be done by heat-seal, ultrasonic weld or adhesive.

One could also attach the bottom layer, the storage layer and the contact layer to each other in order to form the storage chamber, but the storage layer will then not be "sealed off" until the top layer is attached to the rest of the layers. The top layer must then be "welded" in exactly the same way as rest of the layers, i.e. around the welt that forms the sealed storage chamber.

As an extra security, in order to protect the device according to the present invention from contaminants such as dust, bacteria, moisture etc. before the use of the device, the different layers are also connected, for instance by adhesion, welding or any other suitable method, around their outer peripheries. This will form a device that is "closed" around its outer edges, except for the pocket opening. The connection can be a simple "weld" or a fluid tight "weld".

The top layer may be manufactured from a plastic film, a laminate or any other suitable material(s), where the material(s) is substantially impermeable.

When the top layer is removed by tearing, the device is ready for use. The product(s) stored in the storage chamber will remain in the storage chamber until the device is subjected to a mechanical pressure.

Before the above described sealed storage chamber is made, the device must be filled with the product(s) it shall accommodate. In order to be able to fill the device with a product that is thin and/or have low viscosity, it is created at least one temporary liquid barrier in the device. This temporary liquid barrier is obtained by "welding" the bottom layer and the storage layer together, where the weld seam will form a closed circuit. The temporary liquid barrier is arranged within the sealed storage chamber.

When the temporary liquid barrier is made, one or more needles or nozzles are used to fill the product(s) inside the temporary liquid barrier. The needles or nozzles can then either inject the product directly into the temporary liquid barrier, by being brought into the temporary liquid barrier, or the product(s) can be delivered onto a surface of the storage layer, the needles or nozzles being in contact with the surface or also a distance over the surface.

When the product(s) is delivered into the temporary liquid barrier, the product(s) will, due to its low viscosity, almost immediately begin to flow out. However, the temporary liquid barrier will delay the product(s) to run over the weld seam of the barrier. This delay will give enough time to form the above described sealed storage chamber. This sealed storage chamber is a fluid tight chamber, and the product(s) will therefore be "trapped" inside the sealed storage chamber and the substantially impermeable bottom layer and top layer.

The temporary liquid barrier must not necessary be a closed barrier, as one may also obtain the desired purpose by spot welding, laying a broken weld seam or combining the two.

If the device according to the present invention is manufactured with more than one storage chamber, one should understand that each of the storage chambers must have a temporary fluid barrier inside it.

The temporary liquid barrier may also be made in other ways, for example by gluing the bottom layer and the storage layer together, where the glue will create an upstanding edge in the two layers. This edge will, when the product(s) is filled inside the temporary liquid barrier in the storage layer, delay the product(s) to run over the edge, whereby this will give time to attach the other layers in order to form the sealed storage chamber, this storage chamber being arranged outside the temporary liquid barrier.

One could also make the temporary fluid barrier as a "basin", where this can be achieved by laying a string of glue, wax or the like directly on the bottom layer and/or the storage layer, where the basin is created when the bottom layer and the storage layer are laid together.

Yet another possible way to make the temporary liquid barrier is to make at least one of the layers thinner in the area that defines the temporary liquid barrier, this creating a sunken area/hollow/hole or "bowl" in the layer(s). When the different layers are laid together, the product(s) will be supplied through the nozzles or the needles. As the product(s) has low viscosity, it will first fill the sunken area/hollow/hole or "bowl", and first thereafter will it flow out over the surface of the layer(s). This will give the desired delay of time in order to be able to create the sealed storage chamber.

One may also combine the above described techniques in order to create the temporary fluid barrier. For instance may the bottom layer and/or storage layer thinned, whereafter they are laid together and welded together.

Even if it above has been described that only the bottom layer and the storage layer are used to create the temporary liquid barrier, it should be understood one or more layers can be included in this process.

The expression "connected" that is used to describe the joining of the different layers of the device should be understood to not only mean a welding or gluing of the layers, but also when at least two layers cooperate, laying adjacent each other, to create the temporary liquid barrier.

The foregoing and other objects, features and advantages of the invention will be apparent from the following, more particular description of preferred non-limiting embodiments of the invention, as illustrated in the accompanying drawings:

FIG. 1 illustrates a principal configuration of a device according to the present invention;

FIGS. 2 and 3 illustrate how devices according to prior art are filled;

FIG. 4 illustrates how a device according to the present invention is filled, and FIG. 5 illustrates a finished device.

In FIG. 1 the principal configuration of a device according to the present invention is shown. The device comprises four different layers, where each layer has its own function.

A bottom layer 4 must prevent the stored product passing through it and is therefore made from a liquid-impermeable material. On its backside, that is the side turning away from a storing layer 3, the bottom layer 4 is joined with an additional elastic pocket layer 5, where these two layers 4, 5, when connected, will form a pocket in the device.

The pocket layer 5 and the rest of the layers 1-4 are, in appropriate ways, connected around their outer peripheries, only leaving a certain area in the pocket layer 5 unconnected, thereby forming an opening between the bottom layer 4 and the pocket layer 5. The user can then put his or her hand into the pocket that is created between the bottom layer 4 and pocket layer 5, when the device is to be used. This pocket will ease the handling of the device and it will also prevent the users hand becoming soiled.

In another embodiment of the present invention, the elastic layer 5 can be replaced with a holding device (not shown), for instance a handle or grip device.

Above the bottom layer 4 a three-dimensional storage layer 3 is arranged. The storage layer 3 contains the liquid and/or colloidal substance that is to be applied onto a desired surface or spot, where the product substance can either be supplied to the storage layer 3 before the different layers 1-4 are connected together, or it can be supplied after the different layers 2-4 are connected together.

The product that is to be contained in the storage layer 3 can for instance be supplied by different kinds of nozzles or needles etc.

Over the storage layer 3 a contact layer 2 is arranged, where this contact layer 2 will allow the liquid and/or colloidal substance to pass through the contact layer 2 from the storage layer 3 and to the surface on which the liquid and/or colloidal substance is to be applied. A side of the contact layer 2 that is facing the surface that is to be applied the liquid and/or colloidal substance is such that it will disperse the liquid and/or colloidal substance evenly and sparsely onto the desired surface or spot.

The device according to the present invention also comprises a top layer 1, where the top layer 1 is manufactured from a substantially impermeable material. The top layer 1 is arranged over the contact layer 2, and will therefore protect the contact layer 2 from fouling during storage and transportation. Before the device is to be used, the top layer 1 must be removed, where this can be done by tearing off the top layer 1. The top layer 1 is therefore formed with a flap or corner, in order to ease the tearing off.

In order to create a storage chamber 8 in the device, in which storage chamber 8 the product is to be contained, the bottom layer 4, storage layer 3, contact layer 2 and the top layer 1 are welded 6 together around an inside of their outer periphery. The storage chamber 8 is a closed chamber and the weld 6 will make it fluid tight. The weld can for instance be done by heat-seal, ultrasonic weld or adhesive.

As an extra security, in order to prevent fouling of the contact layer 2, the different layers 1-5 of the device are also joined around their outer edges. This joining or "weld" must not be a fluid tight connection.

FIGS. 2 and 3 show how devices according to prior art are filled.

In FIG. 2 is shown how a device according to prior art is filled. The device comprises a bottom layer 4, storage layer 3 and contact layer 2. The layers 2-4 are welded together in order to create a storage chamber 8. The weld 6 is laid inside the outer periphery of the layers 2-4. The liquid and/or colloidal substance that is/are to be contained in the storage chamber 8 is then supplied into the storage chamber 8 through needles or nozzles 7.

When the storage chamber 8 has been filled with the liquid and/or colloidal substance, the top layer 1 (not shown in FIG. 2) is joined to the layers 2-4, thereby creating a sealed construction.

One further other embodiment known from prior art is shown in FIG. 3, where the device is comprised of a bottom layer 4, storage layer 3 and contact layer 2, which layers 2-4 are connected as described with reference to FIG. 2. The layers 2-4 are then "wrapped up" between two top layers 1, the top layers being welded 9 on the inside of their outer peripheries, in order to form a fluid tight device.

It can be seen from FIG. 4 how a device according to the present invention is manufactured. In order to be able to fill the device with a product that is thin and/or has low viscosity, a temporary liquid barrier is created in the device. This temporary liquid barrier is obtained by "welding" a bottom layer 4 and a storage layer 3 together, where the "weld" seam or band 10 will form a closed circuit. The temporary fluid barrier is arranged to be inside the storage chamber 8 when this storage chamber 8 is made.

The purpose of the temporary liquid barrier is to delay the product running over the temporary barrier, where this delay will be sufficient to create the storage chamber 8 in the device.

In order to fill the liquid inside the temporary liquid barrier, a nozzle or needle 7 is used. The needle or nozzle 7 can then either inject the fluid directly into the storage layer 3, the needle or nozzle 7 being brought into the storage layer 3, or deliver the fluid onto a surface of the storage layer 3, the needle or nozzle 7 being in contact with the surface of the storage layer 3 or being placed in a distance above the storage layer 3.

The width of the welding seam 10 of the temporary liquid barrier will depend on the liquid and/or colloidal substance that is to be stored in the storage layer 3, as the welding seam acts as a flood control. Typically the width of the welding seam will be in the range of 0.5-2 mm.

It is to be understood that the form of the temporary liquid barrier can be varied, all from being a circle to complex curves, but the liquid barrier will always be a closed circuit.

Furthermore, the temporary liquid barrier may also form several closed compartments in the storage layer 3, which is useful when the device is to contain more than one liquid and/or colloidal substance.

Due to the characteristics of the liquid and/or colloidal substance (for instance weight and capillary forces), the liquid and/or colloidal substance will disperse within the temporary liquid barrier, and the liquid and/or colloidal substance will also disperse over the temporary liquid barrier in the storage layer 3. However, further dispersion of the liquid will be limited by the fluid tight weld 6 of the storage chamber 8.

After the liquid and/or colloidal substance has been filled into the compartment(s) in the storage layer 3, a contact layer 2 and a top layer 1 is placed over the storage layer 3 and pocket layer 4, whereafter the different layers 1-4 are welded together to form the storage chamber 8. The weld 6 is then laid inside and around the outer peripheries of the layers.

The invention claimed is:

1. An applicator device containing a product, the product being a liquid or colloidal substance which device comprises a bottom layer and a top layer, between which two layers at least one layer is arranged, the bottom layer, top layer and the at least one layer being joined around an inside of their outer peripheries in order to create at least one sealed storage chamber in the device, where the sealed storage chamber accommodates the product to be applied, said layers further being connected around their outer peripheries, characterized in that the bottom layer and the at least one layer are connected to create a temporary liquid barrier inside the storage chamber prior to the filling of the product, the temporary liquid barrier slowing the radially outward migration of the product over the temporary liquid barrier.

2. The device according to claim 1, wherein the layers that are joined together to form the storage chamber form an impermeable barrier to the product accommodated in the storage chamber.

3. The device according to claim 1, wherein the temporary liquid barrier is arranged in determined patterns on a portion of or an entire surface of the storage chamber.

4. The device according to claim 1, wherein the bottom layer and the top layer are manufactured from a material substantially impermeable to the product.

5. The device according to claim 1, wherein the bottom layer is joined to an elastic pocket layer (5) in order to form a pocket in the device.

6. The device according to claim 1, wherein a storage layer comprises fiber structures in one or more planes, the fiber structures forming cavities containing the product to be applied.

7. The device according to claim 1, wherein the top layer is welded with weakened zones to a contact layer, a storage layer and the bottom layer.

8. The device according to claim 1, wherein a contact layer, the bottom layer and the at least one layer are connected to create the temporary liquid barrier.

9. The device according to claim 1, wherein the at least one layer comprises a storage layer and a contact layer, the sealed storage chamber being formed by joining the bottom layer, the storage layer, the contact layer and the top layer.

10. The device according to claim 1, wherein the temporary liquid barrier is a weld seam formed in a closed loop.

11. The device according to claim 1, wherein the temporary liquid barrier is a weld formed by spot welding, continuous welding, broken weld or a combination thereof.

12. The device according to claim 1, wherein a hollow is created in the bottom layer and/or a storage layer.

\* \* \* \* \*